United States Patent [19]

Waldman et al.

[11] Patent Number: 5,677,441
[45] Date of Patent: Oct. 14, 1997

[54] NUCLEOSIDES, NUCLEOTIDES AND OLIGONUCLEOTIDES CONTAINING ENZYMATICALLY CLEAVABLE PROTECTING GROUPS

[75] Inventors: Herbert Waldman, Rheinzabern; Armin Reidel, Bingen; Axel Heuser, Karlsruhe; Klaus Muehlegger, Polling; Herbert Von Der Eltz, Weilheim; Christian Birkner, Uffing, all of Germany

[73] Assignee: Boehringer Mannheim GmbH, Mannheim, Germany

[21] Appl. No.: 326,490

[22] Filed: Oct. 20, 1994

[30] Foreign Application Priority Data

Oct. 20, 1993 [DE] Germany .......... 43 35 729.6

[51] Int. Cl.⁶ .......... C07H 19/06; C07H 19/16; C07H 21/00
[52] U.S. Cl. .......... 536/26.12; 536/26.1; 536/26.8; 536/27.3; 536/28.5; 536/28.53; 536/24.3
[58] Field of Search .......... 536/25.3, 26.1, 536/26.12, 26.8, 24.3, 27.3, 28.5, 28.53; 435/91.1

[56] References Cited

PUBLICATIONS

H. Waldmann et al., "Selective Enzymatic Deprotection of Hydroxy and Amino Groups in Carbonhydrates and Nucleosides", Jan. 1994 The Entire Document pp. 65–67.

Li et al., *Biochemistry*, vol. 28, pp. 5779–5786, (1989).
Resse et al., *Journal of the Chemical Society*, Perkin Trans 1, pp. 1263–1271, (1984).
Brown et al., *Journal of the Chemical Society*, Perkin Transactions 1, pp. 1751–1767, (1989).
Moon et al. *Bulletin of the Korean Chemical Society*, vol. 12, pp. 196–199, (1991).
Xu et al., *Tetrahedron Letters*, vol. 32, pp. 2817–2820, (1991).
B. Chaudhuri et al., *Tetrahedron Letters*, vol. 25, pp. 4037–4040 (1984).
Dineva et al., *Bioorganic and Medicinal Letters*, vol. 3, pp. 2781–2784, (1993).
Waldmann et al., *Synlett*, pp. 65–67, (1994).

*Primary Examiner*—Gary L. Kunz
*Attorney, Agent, or Firm*—Felfe & Lynch

[57] ABSTRACT

Process for the production of oligonucleotides of formula II, in which the exocyclic amino groups of the bases adenine, guanine, cytosine, 7-deazaadenine and 7-deazaguanine carry N-phenylacetyl groups, are used for oligonucleotide synthesis, wherein in a first step a starting nucleotide is bound to a solid carrier, subsequently the desired oligonucleotide is synthesized by stepwise coupling with appropriately activated further monomeric nucleotide building blocks of the general formula I with the above-mentioned meanings, if desired, trivalent phosphorus is oxidized to pentavalent phosphorus during and after the synthesis, the oligonucleotide is cleaved from the carrier and the 5' protecting groups are cleaved off. The phenylacetyl functional groups that protect exocyclic $NH_2$ groups of the bases can be cleaved off in a mild way with penicillin amidohydrolase (EC 3.5.1.11).

8 Claims, No Drawings

NUCLEOSIDES, NUCLEOTIDES AND OLIGONUCLEOTIDES CONTAINING ENZYMATICALLY CLEAVABLE PROTECTING GROUPS

This invention relates to nucleotides and nucleosides derivatives in which the exocyclic amino groups thereof are protected by phenyl acetate groups, as well as the use for the production of oligonucleotides.

Nucleic acid derivatives such as nucleosides and their phosphoric acid esters, the nucleotides, play an important role in nature. There they are of central importance as carriers or transmitters of genetic information.

As knowledge has increased of the molecular biological mechanisms that form the basis for these processes, it has become possible in recent years to work on new combinations of genes see, for example E.-L. Winnacker in "Gene und Klone, eine Einführung in die Gentechnologie, VCH Verlagsgesellschaft Weinheim (1985)". This technology opens new possibilities in many areas e.g. medicine and plant breeding.

Parallel to knowledge of molecular biological processes and relations, there has been a great leap forward, particularly in the past ten years, in the development of chemical synthesis technology in the area of nucleic acids. This was in turn beneficial for the above-mentioned development of genetic engineering as a whole. Thus today it is possible, using chemically synthesized DNA building blocks of defined length and base sequence (so-called oligodeoxynucleotides), to synthesize whole genes with the aid of enzymes (ligases). In the form of so-called "primers", such oligomers serve as starting molecules for the enzymatic synthesis of complementary, double-stranded nucleic acids on a "template", i.e. of a single-stranded nucleic acid with the aid of polymerases. This technique utilizes the PCR method that has become of exceptional importance as a method for the amplification (multiplication) of DNA.

The above-mentioned technique of primed synthesis of nucleic acids is also used in DNA sequencing. Knowledge on the sequence, i.e. on the sequence of bases of particular genes or gene areas of the human genome, offers for example the opportunity of diagnostically detecting genetic defects as well as the prospect of their targeted therapy.

As a very recent diagnostic tool, oligonucleotides are also used in the form of so-called "probes" for the targeted "search" for bacterial or viral infections see Hames et al., (1985) in "Nucleic Acid Hybridisation: A Practical Approach" IRL Press.

The so-called "antisense" technology has become known in recent years as a method which may revolutionize the medical therapy of, above all, viral infections Uhlmann and Peyman (1990) in Antisense Oligonucleotides: A New Therapeutic Principle, Chem. Rev. 90: 543. This technique is based on the idea of blocking the genetic information of a virus and thus preventing further gene expression or viral replication. This inhibition can be accomplished by oligonucleotides which are complementary to sections of the viral genome as a result of which either the messenger RNA function is blocked by the hybridisation, or a transfer of the genetic information is prevented by the formation of triplex structures.

The eminent importance of the chemical synthesis of oligonucleotides is apparent from the following exemplary descriptions. A review of the methods is given, for example, in Oligonucleotides and Analogues: A Practical Approach (1991) (F. Eckstein, publ.), IRL Press at Oxford University Press Oxford, New York, Tokyo.

One of the major problems of these syntheses is due to the structure of the monomeric building blocks of all nucleic acids: the multifunctionality of the heterocyclic bases as well as of the sugar moiety.

The nucleic acid bases adenine, guanine, cytosine and thymine or uracil which occur in all nucleic acids carry exocyclic amino groups which in an unprotected form all lead to massive side reactions during chemical synthesis.

Consequently these functional groups must be provided with suitable protecting groups during oligonucleotide synthesis. Mild and, above all, selective conditions are a prerequisite for this when these protecting groups are introduced into the monomeric synthetic building blocks as well as for the cleavage from the final oligomer after the synthesis is completed. Usually these protecting groups are removed after the synthesis by strongly alkaline conditions.

The exocyclic $NH_2$ groups of the heterocyclic bases adenine, cytosine and guanine are protected for example by the alkali-labile benzoyl or isobutyryl residue. In addition other protecting groups are used to a lesser extent such as dimethylaminomethylidene and phenoxyacetyl groups.

The use of the phenylacetyl group to protect exocyclic $NH_2$ groups is described for example by B. von Reese and Skone, J. Chem. Soc. Perkin Trans. $I_x$: 1263 (1984) or by Moon and Huh Bull, Korean Chem. Soc. 12:, 196 (1991). These phenylacetyl protecting groups are usually removed by treatment with concentrated ammonia solution at a high temperature (50° C.) for several hours. This leads to side reactions; particularly in the case of oligoribonucleotides, cleavage of the internucleotide bond is observed. The use of alkaline cleavage conditions can have a particularly disadvantageous effect on the stability of oligonucleotides and in particular of groups bound to oligonucleotides such as reporter groups such as for example digoxigenin. Such signal groups are generally used in the aforementioned oligonucleotide probes for diagnostic or cell-biological problems.

The object of this invention is therefore to provide nucleotides with protected exocyclic $NH_2$ groups which can be used to synthesize oligonucleotides in a simple and mild manner.

This object is achieved by nucleotides of the general formula I,

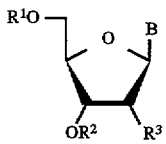

in which B denotes adenine, guanine, cytosine, 7-deazaadenine or 7-deazaguanine, $R^1$ denotes H or an acyl protecting group with 1–4 C atoms or a 4,4'-dimethoxytrityl protecting group, $R^2$ denotes H, an acyl protecting group with 1–4 C atoms, a phosphoramidite or phosphonate residue or a group bound to a solid carrier, $R^3$ represents H, OH or OR' where R' denotes acyl, alkyl or alkenyl each with 1–4 C atoms or a silyl protecting group and the exocyclic amino groups of the bases B are protected by N-phenylacetyl groups.

$R^1$ preferably represents an acetyl group, $R^2$ preferably represents a N,N-dialkylamino-O-(2-cyanoalkyl)phosphane, a H-phosphonate and the solid carrier is preferably controlled pore glass or polystyrene.

Oligonucleotides can be synthesized in the usual manner using these nucleotides. The procedure for oligonucleotide syntheses is generally known to a person skilled in the art and is described for example by Gait, M. J. in Oligonucleotide synthesis, a practical approach, IRL Press, LTD. 1984 and Narang S. A. in Synthesis and application of DNA and RNA, Academic Press 1987.

The invention also concerns oligonucleotides of the general formula II,

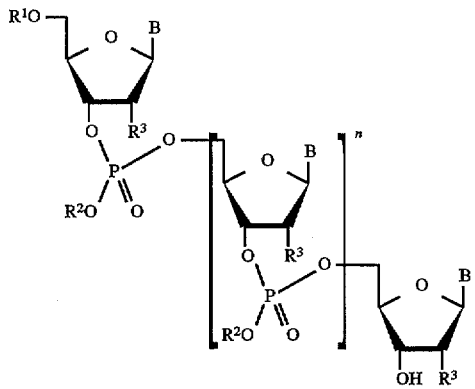

in which B represents nucleic acid bases, $R^1$ denotes H or an acyl protecting group with 1–4 C atoms or a 4,4'-dimethoxytrityl protecting group, and $R^3$ denotes H, OH or OR' where R' preferably denotes acyl, alkyl or alkenyl each with 1–4 C atoms or a silyl protecting group, $R^2$ denotes H, an alkali atom or a protecting group and n denotes a number between 3 and 100, preferably between 6 and 40 and in which the exocyclic amino groups of the bases adenine, guanine, cytosine, 7-deazaadenine and 7-deazaguanine are protected by N-phenylacetyl groups.

Nucleic acid bases are to be understood as the bases generally known to a person-skilled in the art such as e.g. A T G C in which the nucleic acid chains are usually bound N-glycosidically at the 1' position of the sugar.

In addition these oligonucleotides can contain phosphorthioate internucleotide bridges. Such oligonucleotides have great potential in therapeutic applications as so-called "antisense oligonucleotides" since they are extremely resistant to nucleolytic degradation by cellular nucleases. A method of synthesis known to a person skilled in the art is oxidation with sulphur or other known sulphonation reagents such as e.g. tetraethylthiuramdisulfide.

In a preferred embodiment the oligonucleotides are provided with detectable labels (signal group, reporter group). Radioactive labelling is usually carried out with suitable isotopes such as $^{32}P$ or $^{35}S$.

Non-radioactive indicator molecules that have proven to be suitable are inter alia mainly haptens (such as biotin or digoxigenin), enzymes (such as alkaline phosphatase or peroxidase), lumiphores or fluorescent dyes (such as fluorescein or rhodamine) (see e.g. Non-radioactive Labeling and Detection of Biomolecules, C. Kessler (publisher) "Springer Verlag", Berlin, Heidelberg 1992).

Signal molecules can be bound covalently to oligonucleotides by means of reactive functional groups on the oligonucleotide as well as on the respective signal molecule. For example N-hydroxysuccinimide esters of haptens or fluorophores react with 5'-terminal amino functional groups of the oligomers.

In a particularly preferred embodiment the signal groups are introduced as the last step in the oligonucleotide synthesis using phosphoramitides on an automatic synthesizer see Sinha, N. D., in Eckstein F., loc. cit. p. 185 ff.

The invention in addition concerns a process for the production of oligonucleotides of formula II,

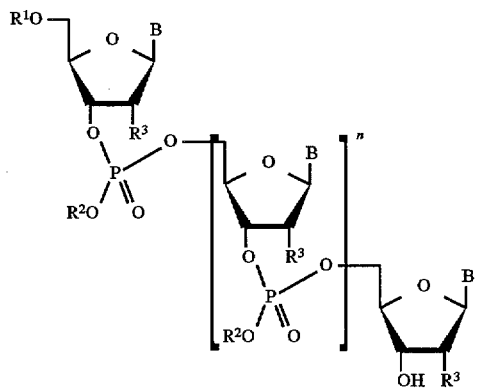

in which B represents nucleic acid bases, $R^1$ denotes H or an acyl protecting group with 1–4 C atoms or a 4,4'-dimethoxytrityl protecting group, $R^2$ represents H, an alkali atom or a protecting group, $R^3$ represents H, OH or OR' where R' preferably denotes acyl, alkyl or alkenyl each with 1–4 C atoms or a silyl protecting group which is characterized in that the nucleotides of formula I with the meanings given there and in which the exocyclic amino groups of the bases adenine, guanine, cytosine, 7-deazaadenine and 7-deazaguanine carry N-phenylacetyl groups are used for the oligonucleotide synthesis and in a first step a starting nucleotide is bound to a solid carrier, subsequently the desired oligonucleotide is synthesized by stepwise coupling with appropriately activated further monomeric nucleotide building blocks of the general formula I with the aforementioned meanings, if desired trivalent phosphorus is oxidized to pentavalent phosphorus during and after the synthesis, the oligonucleotide is cleaved from the carrier and the 5' protecting groups are cleaved off and the phenylacetyl groups are cleaved off by incubation with penicillin amidohydrolase (EC 3.5.1.11).

For this the monomeric synthetic building blocks of the bases are synthesized first in which the reactable exocyclic amino groups of adenine, guanine and cytosine are provided with a phenylacetyl protecting group. The subsequent oligonucleotide synthesis is carried out in a known manner on a solid carrier by the phosphate or phosphite triester method or by the H-phosphonate method. The two latter methods are preferably used in which the synthesis is usually carried out using automated synthesizers.

In this process the reactive nucleotide building blocks (preferably nucleoside phosphoramidites) provided with the appropriate protecting groups are basically—depending on the desired base sequence—continuously coupled in repetitive cycles to a solid carrier provided with a starting nucleoside. Such carriers are preferably inorganic such as e.g. controlled pore glass (CPG) or organic polymers such as e.g. polystyrene. The carrier material usually carries the respective starting nucleoside via a spacer of greater or lesser length which is usually alkali-labile to a greater or lesser degree. The synthesis usually proceeds from the 3' to the 5' end of the oligonucleotide. Before each linkage, the 5' OH protecting group (preferably 4,4'-dimethoxytrityl) is removed by an acid step. If desired, either during or after the synthesis trivalent phosphorus is oxidized to pentavalent phosphorus and non-reacted nucleoside is protected by 5'-O acetylation (capping).

After the synthesis is completed, the product is cleaved from the solid carrier by brief treatment with alkali or organic bases. The phenylacetyl protecting groups are removed enzymatically from the exocyclic amino functional groups by means of penicillin amidohydrolase (Pen-amidase, EC 3.5.1.11). The reaction is preferably carried out for several hours under mild alkaline conditions at pH 7 to 10, particularly preferably at pH values of about pH 8. At room temperature a conversion rate of ca. 85 to 90% is achieved after ca. 3 to 4 hours. The amount of Pen-amidase used is not critical. It is, however, advantageous to use ca. 5 to 100 enzyme units Pen-amidase per mmol oligonucleotide.

In a further embodiment the primary $CH_2OH$ functional group on the sugar moiety can be protected with the very acid-labile dimethoxytrityl(DMTR) protecting group and the 2'-OH group in oligoribonucleotides can be protected with the t-butyldimethylsilyl functional group.

In a preferred embodiment the acid-labile dimethoxytrityl protecting functional group protecting the 5'-OH group is replaced by an enzymatically cleavable protecting group, particularly preferably by acetyl (cleavable with acetyl easters, EC 3.1.1.6). Surprisingly it is possible to selectively cleave the 5'-O-acetyl group from 3,,5'-O-diacetyl-N-phenylacetylated nucleosides with acetyl esterase while retaining the 3'-O-acetyl protecting group. If the nucleosides are only in the 3',5'-O-diacetyl form and not in the N-phenylacetylated form, then acetyl esterase selectively cleaves only the 3'-O-acetyl functional group and the 5'-O-acetyl protecting group is preserved. The production of such partially protected nucleosides is important for numerous relevant syntheses in nucleic acid chemistry.

The invention is elucidated in more detail by the following examples:

EXAMPLE 1

3',5'-Di-O-acetyl-2'-deoxyadenosine 1 g 2'-Deoxyadenosine (3.8 mmol) is suspended in a mixture of 50 ml acetonitrile and 1.4 ml triethylamine (10 mmol), 75 mg 4-dimethylaminopyridine is added to the suspension and, while stirring further, 1 ml acetic anhydride (10.5 mmol) is added. It is stirred overnight at room temperature, 1 ml methanol is added to the reaction solution and it is stirred for a further 10 minutes. The solid is filtered, washed with ethanol and diethyl ether and dried in a vacuum.

Yield: 1.17 g=92% of theory

TLC (silica gel; methanol:ethyl acetate=1:2): $R_f$ 0.51

$^1$H-NMR ($D_2O$): 1.98 and 2.16 (3H, s, 2×$CH_3$), 2.76 (1H, m, $H_{2''}$), 3.00 (1H, m, $H_{2'}$), 4.32 (2H, m, $H_{5'/5''}$), 4.50 (1H, m, $H_{4'}$), 5.50 (1H, m, $H_{3'}$), 6.44 (1H, dd, $H_{1'}$), 8.21 (1H, s, $H_2$), 8.20 (1H, s, $H_8$).

3',5'-Di-O-acetyl-2'-deoxyguanosine is produced in the same manner. 1.37 g of the derivative is obtained in almost quantitative yield.

TLC (silica gel; methanol:ethyl acetate=1:2): $R_f$ 0.47

$^1$H-NMR (DMSO-$d_6$): 1.94 and 1.97 (3H, s, 2×$CH_3$), 2.33 (1H, m, $H_{2''}$), 2.81 (1H, m, $H_{2'}$), 4.11 (2H, m. $H_{4'/5''}$), 4.15 (1H, m, $H_5$), 5.19 (1H, m, $H_{3'}$), 6.03 (1H, dd, $H_{1'}$), 6.40 (2H, bs, $NH_2$), 7.80 (1H, s, $H_8$).

EXAMPLE 2

3',5'-Di-O-acetyl-$N^6$-phenylacetyl-2'-deoxyadenosine

A solution of 3 g phenylacetic anhydride (12 mmol) in 15 ml anhydrous pyridine is added to 1 g 3',5'-di-O-acetyl-2'-deoxyadenosine (3 mmol) and stirred for 2 hours at 120° C. After cooling to room temperature the reaction mixture is poured into 40 ml of a saturated $NaHCO_3$ solution while stirring. It is extracted 6 times with 20 ml dichloromethane each time and the pooled organic phases are dried over $MgSO_4$. After filtering and concentrating in a vacuum, a brown oil is obtained which is purified by means of column chromatography on silica gel (mobile solvent $CHCl_3$/ethanol, 20:1, v/v). The appropriate pure fractions are combined and evaporated.

Yield: 1.18 g=87% of theory

TLC (silica gel; methanol:ethyl acetate=1:2): $R_f$ 0.64

$^1$H-NMR ($CDCl_3$): 2.01 and 2.08 (3H, s, 2×$CH_3$), 2.58 (1H, m, $H_{2''}$), 2.90 (1H, m, $H_{2'}$), 4.14 (2H, s, $CH_2$-Phe), 4.30 (3H, m, $H_{4'}/H_{5'/5''}$), 5.38 (1H, m, $H_{3'}$), 6.40 (1H, dd, $H_{1'}$), 7.33 (5H, m, $CH_2$-Phe), 8.11 (1H, s, $H_2$), 8.63 (1H, s, $H_8$), 8.77 (1H, bs, NH).

3',5'-Di-O-acetyl-$N^2$-phenylacetyl-2'-deoxyguanosine is obtained by means of the same procedure.

Yield: 1.05 g=85% of theory

TLC (silica gel; methanol:ethyl acetate=1:2): $R_f$ 0.59

$^1$H-NMR ($CDCl_3$): 2.08 and 2.11 (3H, s, 2×$CH_3$), 2.49 (1H, m, $H_{2''}$), 2.91 (1H, m, $H_{2'}$), 3.74 (2H, s, $CH_2$-Phe), 4.37 (2H, m, $H_{5'/5''}$), 4.63 (1H, m, $H_{4'}$), 5.38 (1H, m, $H_{3'}$), 6.17 (1H, dd, $H_{1'}$), 7.36 (5H, m, $CH_2$-Phe), 7.72 (1H, s, $H_8$), 9.17 (1H, bs, NH—CO), 11.93 (1H, bs, $N^1$-H).

EXAMPLE 3

Enzymatic hydrolysis of the $N^2$-phenylacetyl protecting group from 3',5'-di-O-acetyl-$N^2$-phenylacetyl-2'-deoxyguanosine 0.95 g 3',5'-di-O-acetyl-$N^2$-phenylacetyl-2'-deoxyguanosine (2 mmol) is dissolved in 25 ml methanol and added to 75 ml of a 0.07M phosphate buffer solution, pH 7.5. It is adjusted to pH 8.0 with 0.1N NaOH and then 100 units penicillin-G-amidase (EC 3.5.1.11) are added. The pH value is kept at 8.0 during the following period by titration with 0.1N NaOH using a pH stat instrument and is recorded by a recording instrument. The conversion rate is about 85%. After extraction with dichloromethane and evaporation, 460 mg 3',5'-di-O-acetyl-2'-deoxyguanosine corresponding to 65% of the theoretical yield are obtained.

The $^1$H-NMR data correspond to those of example 1.

The derivatives 3',5'-di-O-acetyl-2'-deoxyadenosine and -cytidine are obtained by the same process.

EXAMPLE 4

Selective enzymatic cleavage of the 5'-O-acetyl protecting group from 3',5'-di-O-acetyl-$N^2$-phenylacetyl-2'-deoxyguanosine by means of acetyl esterase 0.5 mmol of the diacetylated nucleoside obtained according to example 2 is dissolved in 350 ml 0.15N NaCl solution by stirring for several hours. This is accelerated by treatment with ultrasound. The pH value is adjusted to 6.5 and 10 units acetyl esterase (EC 3.1.1.6) are added. The pH is kept constant by titrating 0.02N NaOH on a combititrator. After the reaction is completed (monitored by means of TLC on silica gel, mobile solvent chloroform/methanol 80:20), the reaction solution is extracted by shaking three times with dichloromethane, the combined organic phases are dried over $Na_2SO_4$ and concentrated in a vacuum. The concentrate is applied to a silica gel 60 column and the desired product is eluted with chloroform/methanol 80:20. The product fractions are pooled and evaporated to an oil. It is taken up in 25 ml dioxane and lyophilized. 3'-O-Acetyl-$N^2$-phenylacetyl-2'-deoxyguanosine is obtained in a yield of 47% as an almost white amorphous powder.

$^1$H-NMR (DMSO-$d_6$): 2.05 (3H, s, CO—CH$_3$), 2.50 (1H, dd, H$_{2'}$), 2.85 (1H, m, H$_{2''}$), 3.32 (2H, m, H$_{5'/5''}$), 3.80 (2H, s, CH$_2$-Phe), 4.04 (1H, m, H$_{4'}$), 5.12 (1H, t, OH$_{5'}$), 5.31 (1H, dd, H$_{3'}$), 6.23 (1H, dd, H$_{1'}$), 7.33 (5H, m, CH$_2$-Phe), 8.27 (1H, s, H$_8$), 11.97 (2H, s, NH—CO).

3'-O-acetyl-N6-phenylacetyl-2'-deoxyadenosine is obtained in an analogous manner from the corresponding deoxyadenosine derivative in a 41% yield.

$^1$H-NMR (DMSO-$d_6$): 2.03 (3H, s, CO—CH$_3$), 2.48 (1H, dd, H$_{2'}$), 2.95 (1H, m, H$_{2''}$), 3.53 (2H, m, H$_{5'/5''}$), 3.82 (2H, s, CH$_2$-Phe), 4.05 (1H, m, H$_{4'}$), 5.12 (1H, t, OH$_{5'}$), 5.35 (1H, dd, H$_{3'}$), 6.40 (1H, dd, H$_{1'}$), 7.30 (5H, m, CH$_2$-Phe), 8.55 (1H, s, H$_8$), 8.60 (1H, s, H$_2$), 10.92 (1H, s, NH).

EXAMPLE 5

Selective enzymatic cleavage of the 3'-O-acetyl protecting group from 3',5'-di-O-acetyl-2'-deoxyguanosine by means of acetyl esteras.

5'-O-acetyl-2'-deoxytguanosine is obtained in a 31% yield by the technique from example 4.

$^1$H-NMR (DMSO-$d_6$): 2.07 (3H, s, CO—CH$_3$), 2.36 (1H, m, H$_{2'}$), 2.76 (1H, m, H$_{2''}$), 3.34 (1H, m, H$_{4'}$), 3.58 (2H, m, H$_{5'/5''}$), 4.01 (1H, m, H$_{3'}$), 5.29 (1H, d, OH$_{5'}$), 6.11 (1H, dd, H$_{1'}$), 6.68 (2H, bs, NH$_2$), 7.91 (1H, s, H$_8$), 11.12 (1H, bs, NH).

5'-O-acetyl-2'-deoxyadenosine is likewise obtained from 3',5'-di-O-acetyl-2'-deoxyadenosine $^1$H-NMR (DMSO-$d_6$): 2.08 (3H, s, CO—CH$_3$), 2.42 (1H, dd, H$_{2'}$), 2.95 (1H, m, H$_{2''}$), 3.63 (2H, m, H$_{5'/5''}$), 4.08 (1H, dd, H$_{4'}$), 5.35 (1H, d, OH$_{5'}$), 5.52 (1H, dd, H$_{3'}$), 6.35 (1H, dd, H$_{1'}$), 7.38 (2H, s, NH$_2$), 8.13 (1H, s, H$_2$), 8.36 (1H, s, H$_8$).

EXAMPLE 6

3',5'-O-(tetraisopropyldisiloxan-1,3-diyl)-2'-deoxyadenosine

The synthesis of this compound is basically carried out according to Markiewicz, J. Chem. Res. (S) 24 (1979) by adding 1.4 ml 1,3 dichloro-1,1,3,3-tetraisopropyldisiloxane (4.4 mmol) to a magnetically stirred suspension of 1.08 g 2'-deoxyadenosine (4 mmol) in 12 ml anhydrous pyridine and stirring the reaction mixture for 5 hours at room temperature. The reaction was complete according to TLC on silica gel in the mixture CHCl$_3$—CH$_3$OH 9:1. After removing the pyridine in a vacuum, the residue was extracted with 100 ml each of CHCl$_3$ and saturated aqueous NaHCO$_3$ solution. The aqueous phase was extracted by shaking twice with 50 ml CHCl$_3$ each time, the organic phases were combined, dried over Na$_2$SO$_4$ and evaporated in a vacuum. After being taken up in CHCl$_3$, it was applied to a short silica gel column and separated initially with chloroform and then with chloroform-methanol. The clean fractions were pooled and evaporated to a solid, foamy residue.

Yield: 1.88 g=95% of theory

TLC (silica gel; chloroform-ethanol 20:1): R$_f$ 0.36

1H-NMR (CDCl$_3$): 1.06 (30H, m, (CH$_3$)$_2$CH), 2.68 (2H, m, H$_{2'/2''}$), 3.88 (1H, m, H$_{4'}$), 4.04 (2H, m, H$_{5'/5''}$), 4.94 (1H, m, H$_{3'}$), 5.80 (2H, bs, NH$_2$), 6.92 (1H, dd, H$_{1'}$), 8.03 (1H, s, H$_2$), 8.31 (1H, s, H$_8$).

3',5'-O-(tetraisopropyldisiloxan-1,3-diyl)-2'-deoxyguanosine and 3',5'-O-(tetraisopropyldlsiloxan-1,3-diyl)-2'-deoxycytidine are obtained by the same process.

Yield of d-guanosine derivative: 1.32 g=65% of theory.
TLC (silica gel; chloroform-ethanol 20:1): R$_f$ 0.18
Yield of d-cytidine derivative: 1.06 g=57% of theory.
TLC (silica gel; chloroform-ethanol 20:1): R$_f$ 0.24

EXAMPLE 7

3',5'-O-(Tetraisopropyldisiloxan-1,3 diyl)-$N^6$-phenylacetyl-2'-deoxyadenosine

The compound was obtained according to example 2 by reacting 0.99 g (2 mmol) of the 3',5'-O protected nucleoside from example 6 with 2.03 g phenylacetic anhydride (8 mmol) in 15 ml anhydrous pyridine. Chromatography was carried out on silica gel H firstly with dichloromethane then with chloroform.

Yield: 0.856 g=87% of theory.

TLC (silica gel; chloroform-ethanol 20:1): R$_f$ 0.70

Elemental analysis (C$_{30}$H$_{45}$N$_5$O$_5$Si$_2$): C$_{cal}$58.93; H$_{cal}$7.36; N$_{cal}$11.45; C$_{found}$59.2; H$_{found}$7.55; N$_{found}$11.1

$^1$H-NMR (CDCl$_3$): 1.05 (28H, m, (CH$_3$)$_2$CH), 2.70 (2H, m, H$_{2'/2''}$), 3.89 (1H, m, H$_{4'}$), 4.03 (2H, d, H$_{5'/5''}$), 4.20 (2H, s, CH$_2$-Phe), 4.95 (1H, m, H$_{3'}$), 6.30 (1H, dd, H$_{1'}$), 7.33 (5H, m, CH$_2$-Phe), 8.17 (1H, s, H$_2$), 8.59 (1H, bs, NH), 8.66 (1H, s, H$_8$).

The corresponding $N^2$-phenylacetyl-2'-deoxyguanosine and $N^4$-phenylacetyl-2'-deoxycytidine derivatives are obtained in an analogous manner.

EXAMPLE 8

$N^6$-phenylacetyl-2'-deoxyadenosine 3 g (5 mmol) 3',5'-O-(tetraisopropylsidiloxan-1,3 diyl)-$N^6$-phenylacetyl-2'-deoxyadenosine is dissolved in 20 ml dry tetrahydrofuran (THF) and 10 ml of a 1.1M tetrabutylammonium fluoride solution in THF is added while stirring. After ca. 10 min the thin layer chromatogram (silica gel, ethanol/chloroform 10:90) indicates the almost complete cleavage of the silyl protecting group (R$_f$ ca. 0.2, starting material ca. 0.5). The reaction is stopped by addition of 25 ml of a mixture of pyridine/methanol/water (3:1:1) and stirred for 30 minutes at room temperature. The solution is evaporated to an oil in a vacuum, taken up in a small amount of ethanol and applied to a silica gel column. After elution with chloroform/ethanol 90:10 the product fractions are pooled, dried over Na$_2$SO$_4$ and concentrated.

Yield: 1.43 g=80.1% of theory $N^2$-phenylacetyl-2'-deoxyguanosine and $N^4$-phenylacetyl-2'-deoxycytidine are obtained in an analogous manner.

EXAMPLE 9

5'-O-(4,4'-Dimethoxytrityl)-$N^6$-phenylacetyl-2'-deoxyadenosine 1.25 g $N^6$-phenylacetyl-2'-deoxyadenosine (3.5 mmol) from example 8 is dissolved in 25 ml dry pyridine and the solvent is removed in a vacuum. This procedure is repeated twice, the residue is then dissolved in 50 ml anhydrous pyridine and 1.75 g 4,4'-dimethoxytriphenylmethyl chloride (5.25 mmol) and 0.9 ml diisopropylethylamine (5.25 mmol) are added successively. It is stirred for ca. 3 hours at room temperature, the reaction solution is then poured into 100 ml 5% aqueous NaHCO$_3$ and it is extracted twice with 100 ml dichloromethane each time. After drying the pooled organic phases over Na₂SO₄ it is evaporated, coevaporated three times with toluene and finally purified on silica gel 60 by means of flash chromatography (column 6×15 cm, dichloromethane-methanol 98:2, 1% triethylamine). The product fractions are pooled, dried and evaporated to form a pale yellow foamy residue.

Yield: 1.7 g=73.9%

TLC (silica gel; dichloromethane-methanol 95:5): $R_f$ 0.75

The 4,4'-dimethoxytrityl derivatives of $N^2$-phenylacetyl-2'-deoxyguanosine and $N^4$-phenylacetyl-2'-deoxycytidine are obtained in an analogous process.

EXAMPLE 10

5'-O-(4,4'-Dimethoxytrityl)-$N^6$-phenylacetyl-2'-deoxyadenosine-3'-[2-(cyanoethyl)-N,N-diisopropylphosphoramidite]

57 µl chloro-β-cyanoethoxy-(N,N-diisopropylamino) phosphane (2.55 mmol) is added dropwise during 2 minutes under argon at room temperature to a solution of 1.6 g 5'-O-(4,4'-dimethoxytrityl)-$N^6$-phenylacetyl-2'-deoxyadenosine (2.5 mmol) and 1.3 ml N-ethyldiisopropylamine (7.5 mmol) in dry THF. The reaction is stopped after about 30 minutes by addition of 50 ml 5% aqueous NaHCO₃ solution. The reaction mixture is extracted twice with 50 ml dichloromethane each time, the organic extracts are combined and dried over Na₂SO₄. After evaporation and flash chromatography (silica gel 60; ethyl acetate-dichloromethane-Et₃N 45:45:10), the pure fractions are collected, dried over MgSO₄ and concentrated to an oil. After dissolving in 50 ml dioxane and lyophilizing, the diastereomer mixture is obtained as a cream-coloured product.

Yield: 1.70 g=79% of theory

TLC (silica gel; dichloromethane-EtOAc-Et₃N 45:45:10): $R_f$ 0.58 and 0.60

$^{31}$P-NMR (CDCl₃): 149 ppm and 152 ppm

The phosphoramidites of 4,4'-dimethoxytrityl-$N^2$-phenylacetyl-2'-deoxyguanosine and 4,4'-dimethoxytrityl-$N^4$-phenylacetyl-2'-deoxycytidine are obtained by the same process. The corresponding thymidine derivative is commercially available.

EXAMPLE 11

Production of controlled pore glass (CPG) carrier loaded with 5'-O-(4,4'-dimethoxytrityl)-$N^6$-phenylacetyl-2'-deoxyadenosine The protected nucleoside from example 9 was bound to CPG beads according to standard methods cited in the literature (e.g. Adams, S. P. et al (1983) J. Am. Chem. Soc. 105, 661-663).

The CPG carriers for 2'-deoxyguanosine and 2'-deoxycytidine were produced by the same technique using the completely protected nucleosides obtained according to example 9.

EXAMPLE 12

Solid phase synthesis of an oligodeoxynucleotide with the sequence d(AATTCCGGAATT) using N-phenylacetyl-protected nucleoside phosphoramidites The synthesis of the oligomer was carried out according to the standard protocol for the phosphoramidite method (Applied Biosystems Users Manual of the DNA synthesizer 380 B) on a 1 µmol scale. After the usual cleavage of the oligonucleotide from the CPG carrier material, the N-phenylacetyl protecting groups were removed very mildly as stated in example 3.

We claim:

1. A compound of formula:

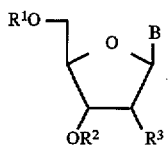

wherein $R^1$ is an acetyl group;

$R^2$ is N, N-dialkylamino-O-(2-cyanoalkyl)-phosphane, an H-phosphonate, a controlled pure glass solid carrier or a polystyrene solid carrier;

$R^3$ is H, OH, OR', wherein R' is C1–C4 acyl, C1–C4 alkyl or C1–C4 alkenyl, or R' is a silyl protecting group, and B is adenine, guanine, cytosine, 7-deazaadenine, or 7-dezaguanine, wherein each exocyclic amino group of B is bound to an N-phenylacetyl group.

2. The compound of claim 1, wherein $R^2$ is N-N-dialkylamino-O-(2-cyanoalkyl)-phosphane.

3. The compound of claim 1, wherein $R^2$ is H-phosphonate.

4. The compound of claim 1, wherein $R^2$ is a controlled pure glass solid carrier or a polystyrene solid carrier.

5. An oligonucleotide of formula

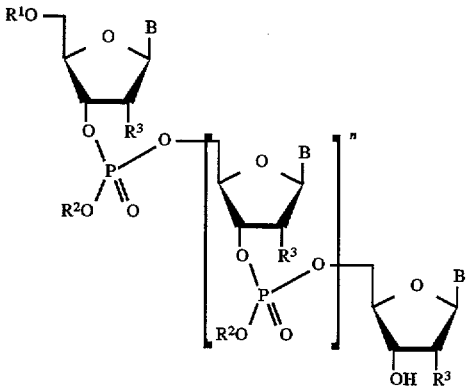

wherein $R^1$ is an acetyl group, $R^2$ is H, an alkali atom or a protecting group, $R^3$ is H, OH, or OR' wherein R' is C1–C4 acyl, C1–C4 alkyl, or C1–C4 alkenyl, or R' is a silyl protecting group, n is a number between 3 and 100, and B is adenine, guanine, cytosine, 7-deazaadenine or 7-deazaguanine, wherein each exocyclic amino group of B is bound to an N-phenylacetyl group.

6. An oligonucleotide having the formula

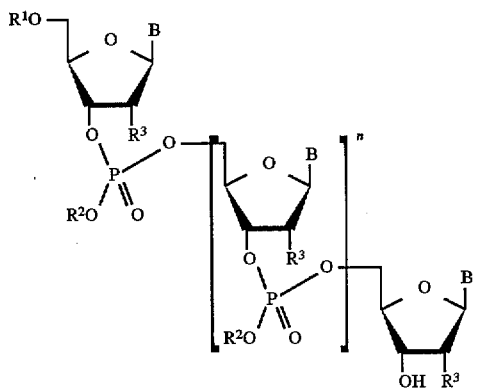

wherein
$R^1$ is an acetyl group,
$R^2$ is H, an alkali atom or a protecting group,
$R^3$ is H, OH, or OR' wherein R' is C1–C4 acyl, C1–C4 alkyl, or C1–C4 alkenyl, or R' is a silyl protecting group,
n is a number between 3 and 100, and
B is adenine, guanine, cytosine, 7-deazaadenine or 7-deazaguanine, wherein each exocyclic amino group of B is bound to an N-phenylacetyl group, with at least one reporter group being attached to at least one nucleotide in said formula.

7. The oligonucleotide of claim 5 in which n is a number between 6 and 40.

8. The oligonucleotide of claim 6 in which the reporter group is selected from the group consisting of a hapten, a fluorophone and a luminophore.

* * * * *